United States Patent [19]

Sepetka

[11] Patent Number: 4,955,862
[45] Date of Patent: Sep. 11, 1990

[54] CATHETER AND CATHETER/GUIDE WIRE DEVICE

[75] Inventor: Ivan Sepetka, Mountain View, Calif.

[73] Assignee: Target Therapeutics, Inc., San Jose, Calif.

[21] Appl. No.: 355,500

[22] Filed: May 22, 1989

[51] Int. Cl.$^5$ ............................................. A61M 25/01
[52] U.S. Cl. ..................................... 604/164; 604/280; 604/282; 128/658
[58] Field of Search ............... 604/280, 282, 264, 93, 604/95; 128/657, 658

[56] References Cited

U.S. PATENT DOCUMENTS

4,368,730  1/1983  Sharrock ............................. 604/164
4,636,346  1/1987  Gold et al. ........................... 604/280
4,676,229  6/1987  Kraznicki et al. ................... 604/282
4,784,639  11/1988  Patel .................................... 604/280

Primary Examiner—Stephen C. Pellegrino
Attorney, Agent, or Firm—Irell & Manella

[57] ABSTRACT

A catheter and catheter device for accessing a target site along a tortuous, small-vessel pathway. The catheter includes a flexible distal segment which is composed of a flexible outer tube and a low-friction surface structure embedded in the polymer tube and forming hard, disjoint surface regions. The surface structure allows the catheter to be advanced over sharp bends and small-diameter loops in a guide wire, in advancing the catheter along a small-vessel pathway.

17 Claims, 3 Drawing Sheets

CATHETER AND CATHETER/GUIDE WIRE DEVICE

1. FIELD OF THE INVENTION

The present invention relates to an improved catheter and catheter device for accessing a tissue target site along a tortuous path through small vessels.

2. BACKGROUND OF THE INVENTION

Catheters are being used increasingly as a means for delivering diagnostic or therapeutic agents to internal target sites that can be accessed through the circulatory system. For example, in angiography, catheters are designed to deliver a radio-opaque agent to a target site within a blood vessel, to allow radiographic viewing of the vessel and blood flow characteristics near the release site. For the treatment of localized disease, such as solid tumors, catheters allow a therapeutic agent to be delivered to the target site at a relatively high concentration with minimum overall side effects.

Methods for producing localized vaso-occlusion in target tissue regions, by catheter injection of a vaso-occlusive agent, have also been described (e.g., U.S. Pat. No. 4,708,718 for "Hyperthermic Treatment of Tumors").

Often the target site which one wishes to access by catheter is buried within a soft tissue, such as brain or liver, and is only reached by a tortuous route through small vessels or ducts —typically less than about 3 mm lumen diameter—in the tissue. The difficulty in accessing such regions is that the catheter must be quite flexible in order to follow the tortuous path into the tissue, and at the same time, stiff enough to allow the distal end of the catheter to be manipulated from an external access site, which may be as much as a meter or more from the tissue site.

Heretofore, two general methods for accessing such tortuous-path regions have been devised The first method employs a highly flexible catheter having an inflatable, but pre-punctured balloon at its distal end. In use, the balloon is partially inflated and carried by blood flow into the target site The balloon is continually inflated during placement to replenish fluid leaking from the balloon. A major limitation of this method is that the catheter will travel in the path of highest blood flow rate, so many target sites with low blood flow rates cannot be accessed.

In the second prior art method, a torqueable guide wire and catheter are directed as a unit from a body access site to a tissue region containing a target site. The guide wire is bent at its distal end and may be guided, by alternately rotating and advancing the wire along a vessel pathway to the target site. An important advantage of this method is the ability to control the location of the catheter along a tortuous path.

It is frequently desirable, for example, in treating deep brain vessel abnormalities, to direct a small-diameter catheter along a tortuous, small-diameter pathway to the target site. The procedure may be advisable, for example, in treating an arteriovenous malformation, in order to introduce an embolic agent into the small capillaries connecting the arterial and venous vessels at a deep brain site. At a certain point along the pathway, when sharp bends are first encountered, the catheter is advanced by alternately guiding the flexible-tip portion of the guide wire along the path, then threading the catheter over a portion of the advanced wire region.

One problem which may be encountered, as the guide wire and catheter are alternately advanced along the tortuous pathway, is the catheter locking against the guide wire. Typically, the problem arises when a sharp bend, sometimes as much as a hairpin loop, is encountered and/or where two or more sharp bends occur in succession. When the catheter and wire become locked together in the region of wire bending, frequently the catheter can neither be advanced nor withdrawn over the wire. In this event, the wire and catheter must be pulled back along the pathway until both are straight enough to allow the wire to be moved axially within the catheter, and often the physician may have to give up attempting to reach the site.

The problem of advancing a catheter over a guide wire in a region of sharp wire bend(s) has been partially solved by the catheter construction disclosed in U.S. Pat. No. 4,739,768. The catheter construction includes a relatively long, less flexible proximal segment, and a shorter, more flexible distal segment having a length of at least about 5 cm. The catheter proximal segment provides sufficient torqueability and axial stiffness for guiding the catheter and internal guide wire from a body access site to the target tissue of interest. Once the tortuous tissue pathway is reached, the more flexible end segment allows the end region of the catheter to be advanced axially over sharper and/or more frequent wire bends without locking on the wire.

Ideally, for accessing the most remote deep-tissue sites, the catheter should be advanceable over a guide wire, even when the wire is forced into a small-diameter loop or a series of closely spaced loops, without locking.

SUMMARY OF THE INVENTION

Accordingly, the present invention provides a catheter which can be advanced over convoluted wire configurations, including small-diameter loops without locking.

The invention also provides a catheter device for accessing deep-tissue target sites along a tortuous pathway containing sharp bends and/or loops.

The catheter of the invention is designed for use in combination with a guide wire for accessing a target site in an internal body tissue, along a tortuous, small-vessel pathway within the tissue. The catheter is formed of an elongate tubular member having proximal and distal ends, and an inner lumen extending between these ends, with a lumen diameter of less than about 40 mils.

The tubular member includes a relatively flexible distal segment at least about 5 cm long for tracking the wire along the tortuous path. The distal segment is composed of a flexible polymer tube and a flexible surface structure embedded within the inner surface of the polymer tube. The surface structure provides a low-friction surface made up of disjoint, relatively non-deformable surface regions arranged to provide uninterrupted contact with a guide wire, as the catheter distal segment is advanced over a looped or bent guide wire region. The surface structure allows the distal segment to be advanced, by remote axial force, over a looped smooth-surfaced guide wire whose loop diameter is substantially smaller than that of the smallest loop over which a flexible polymer tubing having a smooth inner wall surface can be advanced by remote axial force.

Where the catheter is used for accessing a tissue target site from a remote body access site, the tubular member also preferably includes a relatively long, relatively stiff proximal segment which is adapted for advancing the catheter from the body access site to a position at or near the target-site tissue. The proximal segment of the tubular member may be formed of inner and outer coaxial tubes, the outer one of which is more flexible and extends beyond the distal and of the inner tube, to form the flexible polymer tube in the distal segment.

In one preferred embodiment, the surface structure in the distal segment is a closely wound helical wire coil having an inner diameter of between about 8–30 mils, preferably formed from platinum, tungsten, gold, or alloys thereof.

A catheter device constructed according to the invention includes a flexible guide wire in combination with the above catheter. In one preferred embodiment, the guide wire has a distal end region which is encased in a wire coil, and a smooth-walled intermediate region adjacent the distal end region which is in contact with the distal segment in the catheter during a catheter placement operation.

These and other objects and features of the invention will become more fully apparent when the following detailed description of the invention is read in connection with the accompanying drawings.

DETAILED DESCRIPTION OF THE INVENTION

Figure 1:
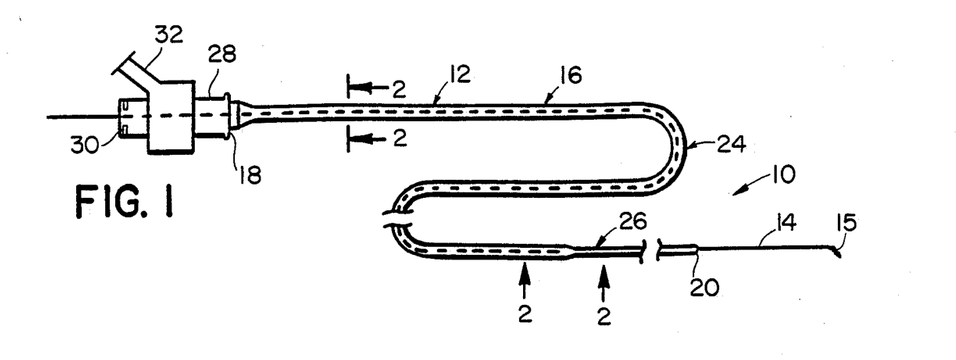
FIG. 1 shows a catheter device which includes a catheter constructed according to the present invention.

FIG. 1 shows a catheter device 10 constructed according to one embodiment of the present invention. The device includes a catheter 12 which will be described below, and a guide wire, here indicated at 14, which typically contains an angled bend 15 at its distal end. The device is designed for accessing a target site which can be reached only along a small-lumen tortuous path within a target tissue, as will be described with reference to FIG. 7 below.

With continued reference to FIG. 1, the catheter includes an elongate tubular member 16 having proximal and distal ends 18, 20, respectively. The tubular member is preferably between about 50–300 cm in length, typically between about 100–200 cm in length An inner lumen 22 (FIG. 2) extending between the two ends has a preferred diameter of less than about 40 mil, and preferably between about 12–30 mil. In one embodiment, the diameter of the inner lumen is between about 2–7 mils greater than that of the guide wire carried within the catheter. The lumen may have a substantially uniform cross-sectional area along its length, or may vary along the catheter length, for example, in a distal end taper. It will be appreciated that the tapered construction may require a similar taper in the diameter of the guide wire, to maintain suitable clearance between the guide wire and catheter.

As will be described in greater detail below, the tubular member includes a relatively stiff proximal segment or segment means 24 terminating proximally at end 18, and a relatively more flexible distal segment or segment means 26 terminating distally at end 20. The distal segment is at least about 5 cm long, typically between about 5–25 cm in length, with the proximal segment providing the remainder of the length of the catheter tubular member. Typically, the proximal segment makes up between about 70%–95% of the total length of the tubular member, and the relatively flexible distal segment makes up the remaining 5%–30% of the length.

The catheter includes a proximal end fitting 28 through which the guide wire is received, and through which fluid material can be introduced into the catheter lumen. One standard fitting which is suitable has a guide wire O-ring seal 30 which can be compressed to provide a suitable seal about the guide wire, while still allowing the wire to be rotated (torqued) and advanced or retracted axially within the catheter, during a catheter placement operation. Fluid material can be introduced into the catheter lumen, for example, from a syringe, through a nozzle 32.

Although the catheter embodiments described herein each include a relatively stiff proximal segment and a relatively include a relatively stiff proximal segment and a relatively more flexible distal segment, it will be recognized that the catheter may be composed of a tubular member with substantially uniform flexibility along its length, and having the construction described below for the distal segment. Such a catheter will typically have a length between about 20–50 cm, and may be used, for example, to access a deep brain site from an access site on or near the neck.

A. Catheter Construction

Figure 2:
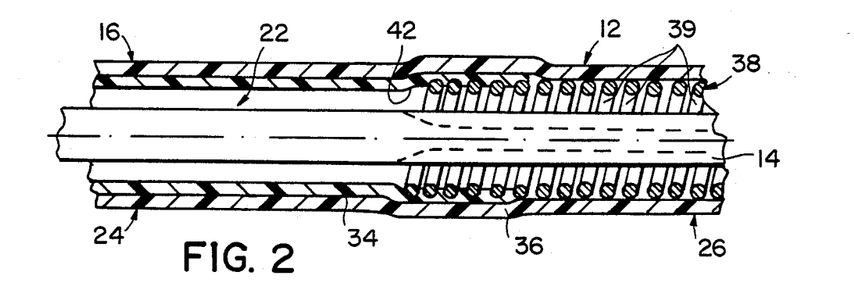
FIG. 2 is an enlarged, sectional view of the catheter device, taken along the region 2—2 in FIG. 1, and having a distal-segment coil structure.

FIG. 2 shows an enlarged cross sectional view of a region of catheter 10 indicated by arrows at 2—2 in FIG. 1, i.e., at the interface between proximal segment 24 and distal segment 26. As seen in the figure, segment 24 is composed of inner and outer coaxial tubes 34, 36, respectively, which are tight-fitting with respect to each other. The stiffness in the proximal segment is provided preferably polypropylene or high-density polyethylene tubing having a final wall thickness (in the assembled catheter) of between about 2-4 mils. The outer, more flexible tube is preferably low density polyethylene or silicone tubing, also having a preferred wall thickness of between about 2-4 mils. As defined herein, high- and low-density polyethylene have the usual trade meaning which is applied to the density grade of polyethylenes which are commonly used in extrusion.

It will be recognized that other tubing materials whose wall thickness can be adjusted to give comparable tubing flexibilities will be suitable, with the constraint that the total wall thickness of the proximal segment should be less than about 10 mils, and that the number of tubing layers of constant or varying flexibility forming the segments, or portions thereof, can be varied to achieve desired flexibility properties in the tube. As an example, the proximal and distal segments may each be formed as a single layer tube, and joined together at the interface by suitable chemical adhesion and/or by overlapping the two tubes in a short interface region.

According to an important feature of the invention, the proximal segment in the catheter is composed of a flexible outer polymer tube—in the present embodiment, the distal extension of tube 36—and a flexible surface structure or means provided, in catheter 12, by a flexible helical wire coil 38 which is encased or embedded in the polymer tube.

Coil 38 is a flexible, helical metal coil whose windings, such as windings 39, are preferably formed of a radio-opaque wire strand material, such as platinum, tungsten, or gold, or alloys thereof, although other materials such as stainless steel, ferromagnetic material, or hard-surfaced polymers may be used. The spacing between windings in the coil is preferably between about 30-70% of the thickness (diameter) of the coil windings, as discussed in Section II below.

More generally, the spacing between windings in the coil is such that the individual windings provide disjoint or spatially separated, relatively non-deformable, i.e., hard-surfaced, surface regions arranged to provide uninterrupted contact with a guide wire, as the distal segment of the catheter is advanced over a looped or bent guide wire region. That is, the coil windings serve to prevent contact between the guide wire and inner surface of tube 36, as the distal catheter segment is advanced over a looped or bent portion of the guide wire. As will be seen below, the flexible surface structure provided by the coil allows the catheter's distal segment to be advanced over a looped guide wire whose loop diameter is substantially smaller than that of the smallest loop over which tube 36 alone can be advanced.

Coil 38 preferably extends along the entire length of the distal segment, but may alternatively terminate short of the distal catheter end, e.g., 1-2 cm from the catheter end. The coil may have a uniform inner diameter, as shown, or may taper on progressing toward the distal end of the catheter The inner diameter of the coil, at its proximal end region 40, is preferably no smaller than that of the inner diameter of the proximal segment, e.g., between about 12-30 mils. Methods of forming wound helical coils suitable for use herein, such as by winding a platinum thread on a rotating mandrel, are well known. The wire making up the coil windings are preferably circular in cross-section, but may alternatively have an elliptical or otherwise a flattened cross-section.

The catheter can be constructed, according to one method, by molding the distal end of tube 34 with a typically 0.5-1 mm proximal end region 42 of coil 38, as shown in FIG. 2. For example, where the inner tube is formed of molded polypropylene tubing, the end region of the tubing is fused over and between the coil windings, forming an interface which has a slightly reduced stiffness, and little change in the inner or outer diameters of the catheter across the junction.

The outer tube is preferably a heat-shrink material which is placed over the over the coil and inner tube and heat shrunk to form a snug fit over both the inner tube and coil. The coil is now embedded or fixed within the outer polymer tube along the distal segment.

Figure 3:
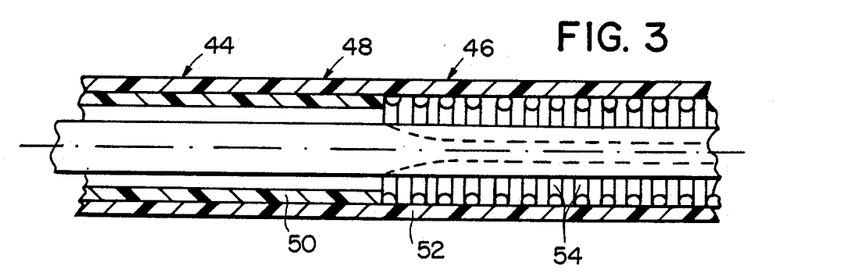
FIG. 3 is an enlarged, sectional view of a catheter device constructed according to another embodiment of the invention, where the catheter has a distal-segment surface structure formed by a series of ridges.

FIG. 3 shows, in an enlarged cross-sectional view, adjoining portions of proximal and distal segments 44, 46, respectively in a catheter 48 formed according to a second embodiment of the invention. The proximal segment is formed of relatively stiff and relatively flexible tubes 50, 52, respectively, as above.

The distal segment in the catheter is formed by the distal extension of tube 52, which has a series of circumferential ridges or rings, such as rings 54, formed on or bonded to the inner surface of the polymer tube. The series of rings in catheter 48 may be hardened polymer or metal rings, or may be formed by coating relatively soft polymer ridges (for example, formed integrally with tube 52) with a hard film material, such as a hard polymer or metal thin film, to give the portion of the rings facing the interior lumen of the segment a hard, relatively non-deformable surface.

The distal portion of tube 52 may be formed, for example, by coating a relatively hard polymer tube with a softer, relatively flexible outer tube. After forming the coaxial tube configuration, the inner tube is treated mechanically or chemically to produce a series of windings or discrete rings supported within, i.e. embedded within, the outer, more flexible coil.

It will be appreciated that the series of hard-surfaced rings form a surface structure which provides disjoint or spatially separated and hard-surfaced or relatively non-deformable regions arranged to provide uninterrupted contact with a guide wire, as the distal segment of the catheter is advanced over a looped or bent guide wire region. The series of rings are also referred to herein as surface means or surface structure providing such non-deformable regions.

Figure 4:
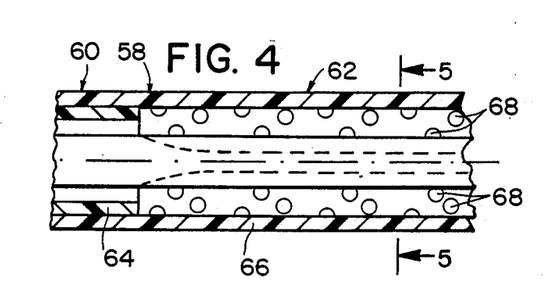
FIG. 4 is an enlarged, sectional view of a catheter device constructed according to a third embodiment of the invention, where the catheter has a distal surface-segment structure formed by an array of substantially non-deformable particles.
Figure 5:
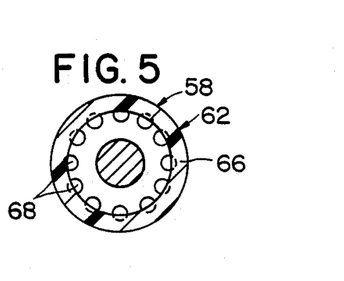
FIG. 5 is cross-sectional view taken along line 5—5 in FIG. 4.

FIGS. 4 and 5 illustrate another embodiment of a catheter 58 constructed according to the present invention. The enlarged cross section i[FIG. 4 shows adjoining portions of proximal and distal segments 60, 62, respectively. The proximal segment is formed of relatively stiff and relatively flexible tubes 64, 66, respectively, as above.

With reference to both FIGS. 4 and 5, the distal segment in the catheter is formed by the distal extension of tube 66, which has an array of hard-surfaced, preferably low-friction particles, such s spheres 68 embedded in the inner surface of the polymer tube. Segment 62 is formed by embedding the particles in the polymer tube, e.g., as the tube is being formed by extrusion. The spheres have preferred diameters of between about 1-3 mils, and are preferably formed of metal or a hard-polymer material.

The surface density of the spheres in the array is such as to insure uninterrupted contact between the spheres and a guide wire, when the distal segment is being advanced over a looped or bent portion of a guide wire. Preferably, the array density is such as to produce sphere-to-sphere contact when the catheter is in a bent configuration (as the distal catheter segment is advanced over a looped or bent guide wire region). Such a surface density of spheres would at the same time limit extreme catheter bending, and thus serve to prevent kinking, as discussed below in Section II.

It can be appreciated that the array of hard-surfaced spherical particles embedded i- the distal segment region of tube 66 form a surface structure which provides disjoint or spatially separated hard-su faced regions arranged to provide uninterrupted contact with a guide wire, as the distal segment of the catheter is advanced over a looped or bent guide wire region. The particle array is also referred to herein a surface means or surface structure for forming such separated regions.

The general two-segment catheter construction can be modified, where desired, for accessing specific types of target areas. For example, to access a target site along a tortuous path which is as much as 25-30 cm in length, the catheter may advantageously include one or more intermediate segments having flexibilities which are intermediate between those of the proximal and distal ends of the catheter. The purpose of the intermediate segment(s) is to provide greater column strength in the distal portion of the catheter which is moved along the tortuous path, but greater flexibility than is provided by the proximal segment of the catheter. The intermediate segment may, but does not necessarily include, flexible surface structure present in the distal end segment of the catheter.

B. Guide wire Construction

Figure 6:
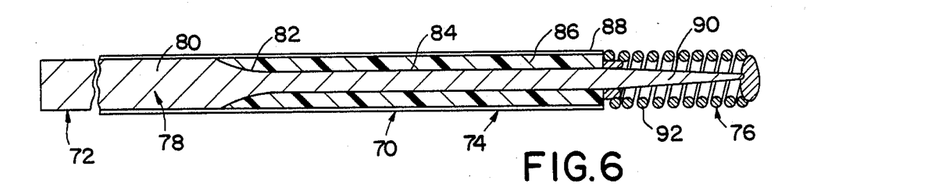
FIG. 6 is an enlarged sectional view of one preferred guide wire in the catheter device of the invention.

FIG. 6 shows a one preferred type of guide wire 70 in a catheter device of the present invention The wire is a flexible, torqueable wire having an overall length of between about 70-300 cm between its proximal and distal ends respectively, and a maximum outer diameter of between about 8-40 mils. The major portion of the wire is a flexible proximal section 72 whose overall length ranges from about 40-250 cm. This section is followed by a more flexible intermediate section 74 having a length between about 15-60 mils, and a most flexible distal end section 76 whose length is between about 1-10 cm. It will be appreciated that the wire is shown in greatly exaggerated radial scale, and that a major portion of the distal end section has been cut away.

A wire core 78 in the guide wire is formed of a flexible, torqueable wire filament material, such as stainless steel. The diameter of the wire core, at its maximum, is between about 8-35 mils. As shown, the segment 80 of the core forming the proximal section of the guide wire has a substantially uniform diameter along its length, and corresponds to the maximum diameter of the core, i.e., between 8-35 mils.

Within the intermediate section of the wire, the core is tapered from the proximal-section diameter down to a reduced diameter which is preferably about 4-20 mils and between about 10%-50% of the core's proximal segment diameter. Thus, for example, where the proximal section core diameter is 18 mils, the core tapers to a minimum of between about 2-9 mils.

In the embodiment shown in FIG. 6, the taper in the core occurs over a relatively short tapered segment 82 which is followed by a reduced-diameter segment 84 having a substantially constant diameter along its length. The 10%-50% that of the constant-diameter, and the two segments together make up the length of the intermediate wire section, i.e., about 20-60 cm.

The two segments 82 and 84 making up the core of the intermediate section of the wire are covered along their length by a flexible polymer covering 86. The covering functions both to provide a smooth outer surface of the intermediate section, and to increase the column strength of the reduced-diameter core in the intermediate section. Covering 86 is preferably formed of a polymer, such as Teflon TM, polyolefin, or polyurethane which can be bonded or otherwise tightly affixed to the core wire. The covering may additionally include a surface coating 88 of a highly lubricous polymer material.

As seen, the thickness of the covering is such that the intermediate segment has substantially the same outer diameters, e.g., between about 8-35 mils as the proximal segment of the guide wire.

With continued reference to FIG. 4, distal section 76 of the wire has a length between about 1-10 cm and preferably has still greater flexibility than the intermediate wire section. The wire core in the distal section, referred to as segment 90, has a diameter which substantially no greater than that of the intermediate section core, and preferably is tapered to a reduced diameter of between about 2-6 mils.

The distal section portion of the core is fully or partially encased in a flexible sleeve 92. The sleeve shown in FIG. 6 is a soft, flexible helical coil which is formed conventionally, e.g., as described above. Where the catheter includes a helical wire coil in its distal segment, the coil at the distal end region of the guide wire is preferably formed with a different pitch angle than the catheter coil, to prevent interlocking of the helical windings in the two coils. It is also noted in this regard that the portion of the guide wire over which the flexible distal segment of the catheter is advanced is predominantly the smooth-walled intermediate section, rather than the coil-encased distal wire segment.

In forming the guide wire of the invention, the wire core is typically constructed by grinding a conventional, constant-diameter guide wire, such as is commercially available stainless steel wire. The flexible polymer tube covering the intermediate core is segment(s) can be applied to the core by conventional polymer spraying or dipping methods, or by attaching a preformed polymer tube to the core segment(s). The latter can be accomplished by attaching the tube to the core under heat shrinking conditions, or by securing tube to the wire by a suitable wire/polymer bonding agent.

It will be appreciated that other guide wire constructions may also be employed. For example, the guide wire may have an extended distal tapered wire segment, and a distal end coil which encases a distal end region of the tapered wire segment.

The guide wire itself must have a relatively small diameter, to permit its guided movement along a tortuous path in a target tissue. In a preferred embodiment of the invention, the inner diameter of the catheter and the outer diameter of the guide wire are substantially constant along their lengths, and the inner diameter of the catheter is between about 2-7 mils greater than the diameter of the core wire. Thus, for example, a guide wire designed for use with a catheter with a constant lumen diameter of between about 20-25 mils may have a preferred diameter of between about 15-18 mils.

II. Test Characteristics

Figures 7, 8:
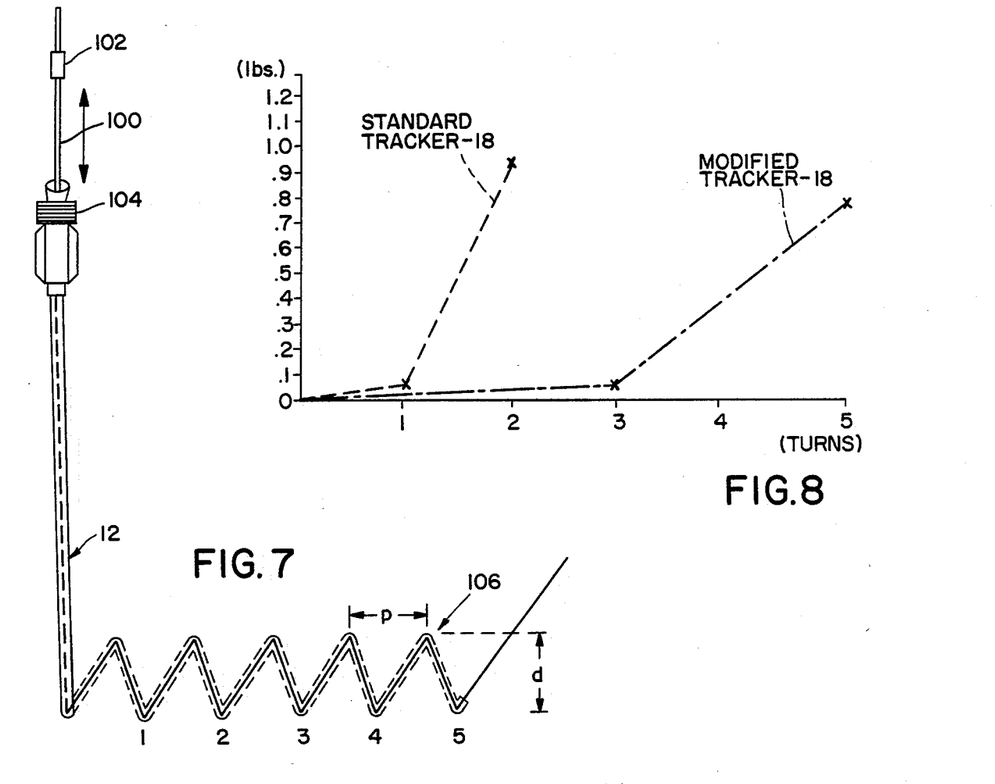
FIG. 7 illustrates a test configuration for measuring the resistance of a catheter being advanced over a guide wire with helical windings.
FIG. 8 shows plots of the force required to advance a standard polymer-tube catheter (dashed lines) and a catheter constructed according to the invention (dash-dot lines) over a smooth-surface wire, as a function of the position of the catheter on the helical wire turns.

The catheter of the present invention is designed for advancement along a guide wire which has been placed, by movement along a tortuous path, in a highly convoluted bent and/or coiled configuration. FIG. 7 illustrates a test configuration for measuring the ability of a catheter of the invention to be advanced along a guide wire containing a series of helical windings.

The guide wire used in this test was a 14-mil stainless steel mandrel 100 having a total length of 175 cm. The proximal end of the mandrel was clamped to the upper jaw 102 of a conventional tensile test device designed to measure the tensile force applied being two jaws 102 and 104, as the jaws are moved relatively toward or away from one another. A distal end portion of the mandrel was formed into a helix 106 having five windings which are numbered in the figure. The helix diameter d was about 10 mm, and the helic pitch p, about 5 mm.

Each catheter that was tested was flushed with saline and back loaded over the mandrel until the catheter's distal end was just upstream of the coiled portion of the mandrel. The proximal catheter end was locked in jaw 104, as shown, and this jaw was moved downwardly with respect to the stationary jaw 102, to advance the distal segment of the catheter over the coiled portion of the mandrel. The tensile force between the two jaws as this movement occurs was measured conventionally, and the force data were recorded on a chart recorder, along with the position of the catheter's tip on the guide wire coil.

The test catheter had a length of 150 cm in length, composed of a 135 cm proximal segment and a 15 cm flexible distal segment, a lumen diameter of 22 mils, and a 22-mil inner diameter platinum coil extending along the length of construction, but without the distal segment coil.

FIG. 8 shows the force in pounds, applied between the jaws in the test device, as the distal end of the catheter is advanced along the helix. The force curve of the catheter of the present invention is indicated by dash-dot line, and that of the control catheter, by dashed line. The data plotted represents the average of three different test runs for each catheter.

As seen from FIG. 8, the catheter of the present invention was able to be advanced over three coil windings with very little force (less than about 0.1 lb). A linearly increasing force was required for advance between the third and fifth coil windings. The catheter could be easily advanced over the five-winding helix and only locked against the guide wire when the proximal segment of the catheter reached the coiled section of the mandrel.

The force curve of the control catheter, shown in dashed lines, indicates the much greater resistance which is encountered in advancing this catheter over the coiled guide wire segment. The control catheter could be advanced only over one coil winding at low force, with a sharp increase in force required in advancing along the second winding. The catheter could not be advanced over two complete guide wire windings.

Figure 9:
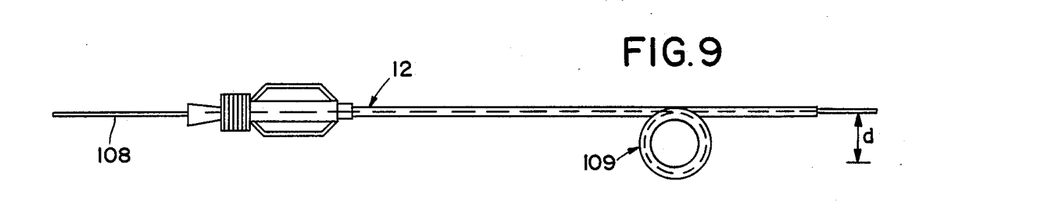
FIG. 9 illustrates a test configuration for determining the smallest diameter wire loop over which a catheter can be advanced.

FIG. 9 illustrates a test configuration to determine the smallest guide wire loop over which a catheter can be advanced. In this test, a 13 mil guide wire (wire mandrel) 108 is formed with a loop 109 of diameter d, which may be between 1-10 mm. A catheter constructed according to the present invention, and a control catheter having the same dimensions as in the helical winding test described above were compared. The catheter of the invention was able to be advanced easily over a guide wire loop having a loop diameter of 2 mm. By contrast, the smallest loop over which the control catheter could be advanced was a 4 mm diameter loop.

Figure 10:
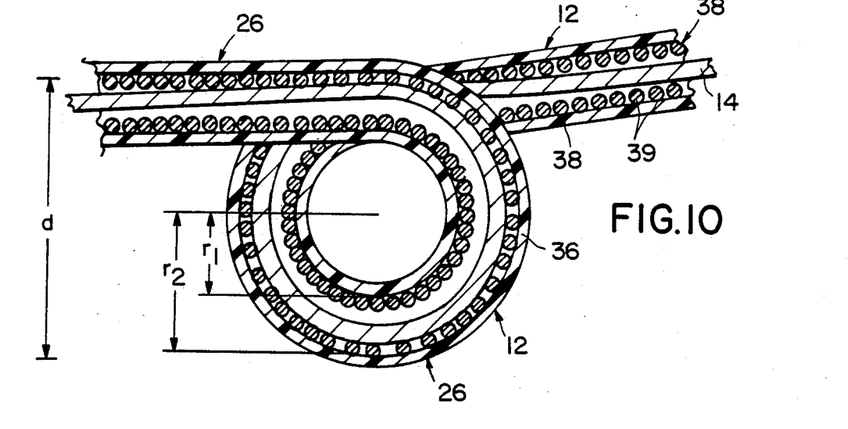
FIG. 10 is an enlarged cross-sectional view of the catheter of the invention being advanced over a looped portion of a guide wire.

FIG. 10 shows, in enlarged cross-sectional view, the portions of the guide wire and catheter in the looped region of FIG. 9, where the guide wire loop diameter d is about 2 mm. The figure illustrates the features of the invention which allow the catheter to advance over a small-diameter guide wire loop. As seen, bending in the catheter, as it is advanced over the guide wire loop, is accommodated by coil expansion on the outer side of the loop, and by coil contraction on the inner side of the loop.

In advancing over the guide wire loop, the catheter tends to straighten or uncoil, forcing the surfaces of the coil windings on the outer side of loop against the guide wire. The coil surfaces in contact with the guide wire provide a series of hard, relatively non-deformable surface regions which substantially reduce the friction between the wire and inner lumen of the catheter as the catheter is moved along the wire by axial force exerted from the proximal end of the catheter.

It will be appreciated from FIG. 10 that the spacing between the coil windings must be small enough to provide uninterrupted contact between the coil windings and the guide wire, when the windings in the outer side of a bend or loop are in an expanded-spacing form, as in the figure. That is, the spacing between windings in this expanded form must not be so large as to permit the guide wire to contact the more flexible outer polymer tube in the distal segment. Such contact would introduce regions of high frictional resistance, due to the deformability of the polymer tube. This, in turn, would lead to high axial forces and may produce locking between the guide wire and catheter, as is characteristic of prior art flexible catheters, such as the control catheter employed in the tests described above.

In addition, the spacing between coil windings is preferably such that coil windings are compressed into contact with one another, as illustrated in FIG. 10, when the catheter is looped or bent at a lower limit of radius of curvature. When this point or winding contact is reached, further bending in the catheter can only be accommodated by displacing one or more of the coil windings toward the interior of the lumen (which can be prevented by bonding the outer surfaces of the coil to the polymer tube inner surface).

In this regard, it is noted that the coil windings also act to prevent kinking in the catheter tube, as the tube is bent or looped. The coil windings accomplish this by preventing the inner and outer sides of the bent catheter tube from collapsing on one another, which characterizes the kinked condition. That is, the coil windings act to resist the strain between the inner and outer sides of a bent region of the catheter which leads to kinking. The action of the windings in resisting catheter kinking will be most effective when the coil windings are substantially contiguous, i.e., in contact, in the inner side of the bent region, thus precluding interwinding regions where kinking might occur.

From the considerations above, an optimal coil winding spacing (in a straight-coil configuration) can be determined, as follows. With reference to FIG. 10, the length l of a section of catheter coil in a straight condition is approximated as the average of the inner and outer tube circumferences of a same coil section in a looped configuration. That is:

$$l = \frac{1}{2}(2\pi r_1 + 2\pi r_2),$$

where $r_1$ and $r_2$ are the inner and outer radii of the coil in the looped condition (FIG. 1).

As an example, it is assumed that the coil has a diameter 0.5 mm (about 20 mils), that the windings have a cross-sectional diameter of 0.05 mm (about 2 mils), and that the smallest diameter loop which the catheter will be allowed to make is about 2 mm. Thus, when the catheter is in a condition of smallest loop the catheter is allowed make, $r_2$ is about 1 mm, $r_1$ is about 0.5 mm, and l, the length of the coil section in a straight condition is calculated to be about 4.7 mm.

From the known inner circumference $2\pi r_1$ of about 3.1 mm, and given that this circumference is composed of n contiguous coil windings, each 0.05 mm in diameter, it is calculated that the looped coil section must be made up of n=62 windings. The total winding spacing in the straight coil section is then 4.7 mm−3.1 mm (the portion of the length contributed by 62 windings, 0.05 mm each), equals 1.6 mm. The spacing between each winding is then 1.6 mm divided by 62, or about 0.025 mm. That is, the coil winding spacing which gives the desired bending characteristics in the catheter coil is about 50% of the thickness or diameter of the windings themselves. Preferred winding spacings in the coil are between about 30–70% of the winding diameters.

It will be appreciated how the above considerations can be applied to the surface structures formed by rings or particles in catheters 44 or 62 above, to determine optimal spacing between the rings or particles.

III. Operation

Figures 11, 12:
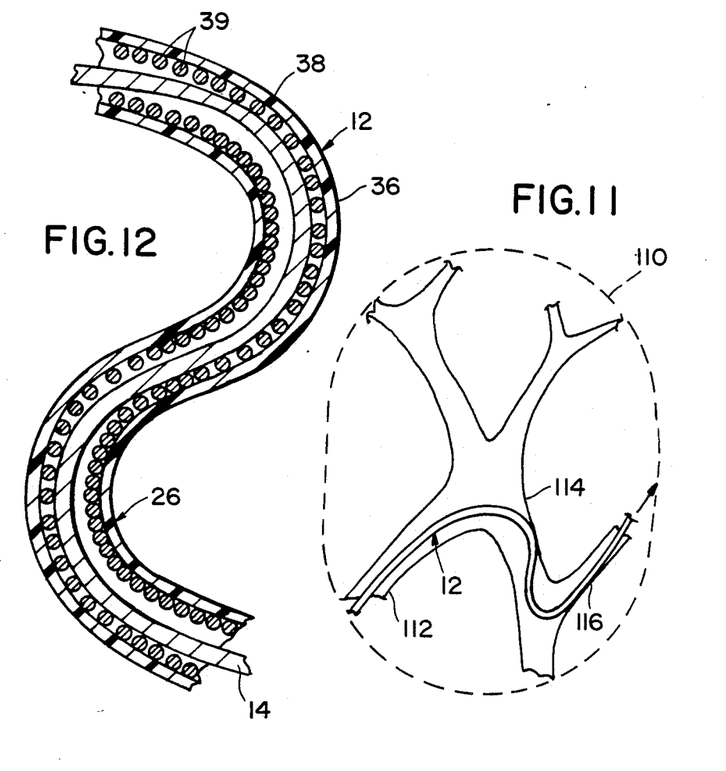
FIG. 11 illustrates a typical small-vessel pathway in which a serpentine configuration is encountered.
FIG. 12 is an enlarged cross-sectional view of the catheter of the invention being advanced over the serpentine portion of a guide wire in FIG. 11.

The operation of the catheter and catheter device of the invention, in accessing a target region along a tortuous, small-vessel path will be described now with reference to FIGS. 11 and 12. FIG. 11 shows a region of soft target tissue 110, such as brain tissue, which includes a portion of a small-vessel, tortuous pathway which must be traversed in reaching a selected target site (not shown). The region shown contains vessel 112 which branches into vessel 114, and a vessel 116 which branches from the lower portion of vessel 114. The vessels may have diameters typically between about 2–5 mm or less, and the both of the junctions connecting vessel 112 with the lower portion of vessel 114, and vessel 114 with vessel 116 are greater than 90 degrees.

To reach region 110, the guide wire and catheter, i.e., the catheter device, are first threaded as a unit from an external access site through the vasculature to a region adjacent, but not into the tortuous path region of the target tissue. This is done in the usual case where the catheter must pass through the cardiac aorta by first placing a relatively large-diameter guiding catheter (e.g., about 40 mils inner diameter) from the access site through the aorta and toward the target site. The catheter and guide wire are then threaded through the guiding catheter past the aorta, where large-vessel diameters and high blood flow volumes make it difficult or impossible to control the movement and position of the catheter.

Once the catheter device is beyond the guiding catheter, into the target tissue, and at a region, such as region 110 or tortuous pathway, the catheter and guide wire must be controlled to move toward the target site. Specifically, the guide wire is advanced independently along the tortuous path in the target tissue, according to standard wire manipulations, which include rotating or torquing the wire at each bend, to orient bend 15 formed in the wire (FIG. 1) toward the next vessel in the pathway.

For example, in FIG. 11, the wire, when it reaches the junction of vessels 112, 114, is torqued to orient the wire bend downwardly, and the wire is then advanced, independent of the catheter, into vessel 114. When the next vessel junction is reached, the wire is torqued in the opposite direction, and advanced from vessel 114 into 116. At some point, for example, when the wire has been advanced a total of 2–8 cm ahead of the catheter, the catheter is then advanced over the wire, to thread the catheter up to a point near the distal end of the guide wire.

The bent region of the catheter and guide wire in FIG. 11 are shown in enlarged sectional view in FIG. 12. Both bends in the catheter device have radii of curvatures corresponding to approximately 2 mm diameter loops, and thus force the coil windings on the inner sides of each bend into contact with one another, lifting the degree of bending which can occur in the catheter.

The more spaced windings on the outer sides of each bend are engaged with the guide wire, as the catheter is advanced over the guide wire, to provide a low-friction contact between the wire and catheter lumen. As detailed above, the reduced friction, due at least in part to the non-deformability of the coil windings, allows the catheter to be advanced over much sharper bends, and with much less axial force, than a flexible polymer tube.

Once the catheter has been advanced to the target site, the guide wire is withdrawn to allow a fluid material to be injected into the site. The low friction feature of the present invention which allows the catheter to be advanced easily along bent portions of the guide also allow the guide wire to be removed easily from the bent and/or looped catheter region along the tortuous vessel path. The material injected via catheter may include: (1) radio-opaque agents for viewing blood vessel anatomy and blood flow characteristics in the target region; (2) vaso-occlusive agents, such as a suspension of collagen fibers. which can be used to produce small-artery vaso-occlusion in the tissue region supplied by the target vessel; and (3) pharmacological agents, such as anti-tumor drugs which are effective against identified disease states at the target site.

From the foregoing, it can be appreciated how various objects and features of the invention are met. The novel catheter construction described herein allows for tracking along a tortuous path over a guide wire containing several loops or bends whose radii of curvature correspond to 2 mm diameter loops or less, with substantially reduced axial force needed in advancing the wire. This feature allows catheter access to a variety of deep tissue target sites which have been inaccessible heretofore because of inability to advance the catheter along the guide wire and/or locking of the catheter with the guide wire in regions of sharp bends.

The flexible surface structure in the distal segment of the catheter can be designed and constructed to prevent catheter kinking, by (a) limiting the curvature of bends in the catheter, and (b) in the case of coil or ring structures, by resisting the tendency of the tube to collapse in a region of sharp bends.

Where the flexible surface structure is a radio-opaque material, such as gold, platinum, or tungsten wire, the distal segment of the catheter can be readily visually fluoroscopically, allowing the user to view the extent of catheter advance over a guide wire and thereby better control the catheter placement operation.

The flexible surface structure may also be employed as a heating element within the target site, by employing for example, a conductive coil which can be heated by an external fluctuating magnetic field. Another advantage of a coil surface structure is the ability to pre-shape the distal segment prior to use to facilitate catheter placement under selected conditions.

The catheter can be easily manufactured using conventional catheter production methods, including coil winding and polymer tube extrusion methods.

While preferred embodiments of the invention have been described herein, it will be recognized that a variety of changes and modifications can be made without departing from the invention.

It is claimed:

1. A catheter for use in combination with a guide wire for accessing a target si-e in an internal body tissue along a tortuous, small-vessel pathway within the tissue, said catheter comprising an elongate tubular member having proximal and distal ends, and an inner lumen extending between these ends, with a diameter which is no greater than about 40 mils, said member including relatively flexible distal segment means at least about 5 cm long adapted for tracking the wire along such tortuous path, said distal segment means being composed of:
(i) a flexible outer polymer tube, and
(ii) flexible surface means embedded in the inner surface of the outer polymer tube providing a surface made up of disjoint, relatively non-deformable surface regions arranged to provide uninterrupted contact with a guide wire, as the distal segment of the catheter is advance over a looped or bent region of a guide wire, allowing the distal segment to be advanced, by remote axial force, over a looped smooth-surfaced guide wire whose loop diameter is substantially smaller than that of the smallest loop over which a flexible polymer tubing having a smooth inner wall surface can be advanced by remove axial force.

2. The catheter of claim 1, wherein the distal segment means is able to be advanced over a guide wire loop having a 2 mm diameter.

3. The catheter of claim 1, wherein said flexible surface means is a wire coil having an inner diameter of between about 8-30 mils.

4. The catheter of claim 3, wherein the coil is formed of windings having a given diameter, and the spacing between adjacent coil windings is between about 30-70 percent of the given winding diameter.

5. The catheter of claim 3, wherein the coil is formed from platinum, tungsten, gold, or alloys thereof.

6. The catheter of claim 1, wherein said flexible surface means includes a series of axially spaced rings embedded in the inner surface of said outer polymer tube, said rings having relatively non-deformable surfaces.

7. The catheter of claim 1, wherein said flexible surface means includes an array of relatively non-deformable particles partially embedded within the inner surface region of the outer polymer tube.

8. The catheter of claim 1, wherein said tubular member further includes proximal segment means extending between said proximal end and the distal segment means, said proximal segment means being relatively longer and stiffer than said distal segment means.

9. The catheter of claim 8, wherein said proximal segment means is formed of inner and outer coaxial tubes, one of which is relatively stiff, and one of which is relatively flexible, and said outer polymer tube in the distal segment means is a distal extension of the relatively flexible tube.

10. The catheter of claim 9, wherein the relatively flexible tube is the outer of the two coaxial tubes, said surface means is a flexible wire coil, said coil has a proximal end which is received in a distal end of the inner tube, and the remainder of the coil is encased in the outer, distal end portion of the more flexible tube which forms the flexible outer polymer tube.

11. A catheter device for accessing a target site in an internal body tissue along a tortuous small-vessel pathway within the tissue, said device comprising a guide wire having proximal and distal ends, and a wire diameter of no greater than about 30 mils, and
a catheter comprising a tubular member having proximal and distal ends, and an inner lumen extending between these ends, with a diameter which is no greater than about 40 mils, said member including relatively flexible distal segment means at least about 5 cm long adapted for tracking the wire along such tortuous path, said distal segment means being composed of
(i) a flexible outer polymer tube, and
(ii) flexible surface means embedded within the inner surface of the outer polymer tube providing a low-inner friction surface made up of disjoint, relatively non-deformable surface regions which are arranged to provide uninterrupted surface contact with a guide wire, as the distal segment of the catheter is advanced over a looped or bent guide wire region, allowing the distal segment to be advanced, by remote axial force, over a looped smooth-surfaced guide wire whose loop diameter is substantially smaller than that of the smallest loop over which a flexible polymer tubing having a smooth inner wall surface can be advanced by remote axial force.

12. The catheter device of claim 11, wherein the distal segment means is able to be advanced over a guide wire loop having a 2 mm diameter.

13. The device of claim 11, wherein the flexible surface means is a closely would helical wire coil having an inner diameter of about 8-30 mils.

14. The device of claim Il, wherein the guide wire has a distal end region which is encased in a wire coil, and a smooth-walled intermediate region adjacent the distal end region which is in contact with the distal segment means in the catheter during a catheter placement operation.

15. The device of claim 14, wherein the smooth-walled intermediate section has an outer surface formed by a lubricous polymer material.

16. The device of claim 11, wherein the inner diameter of said distal segment means is between about 2-7 mils larger than the diameter of the wire's smooth-walled intermediate section.

17. The device of claim 11, wherein said tubular member further includes proximal segment means extending between said proximal end and the distal segment means, said proximal segment means being relatively longer and stiffer than said distal segment means.

* * * * *